United States Patent [19]  
Weisberg et al.

[11] Patent Number: 4,669,491  
[45] Date of Patent: Jun. 2, 1987

[54] COMPOSITIONS AND PROCESS FOR APPLYING PROTECTIVE COVERING AND EXTENSIONS TO FINGERNAILS

[75] Inventors: Renee Weisberg, 1137 Village Circle Dr. S., Phoenix, Ariz. 85022; Lawrence J. Krebaum, Glen Ellyn, Ill.

[73] Assignee: Renee Weisberg, Phoenix, Ariz.

[21] Appl. No.: 680,578

[22] Filed: Dec. 11, 1984

Related U.S. Application Data

[63] Continuation-in-part of Ser. No. 636,987, Aug. 2, 1984.

[51] Int. Cl.$^4$ .............................................. A45D 29/00
[52] U.S. Cl. ..................................... 132/73; 132/88.5; 424/70
[58] Field of Search ........................................... 132/73

[56] References Cited

U.S. PATENT DOCUMENTS

| | | | |
|---|---|---|---|
| 2,288,386 | 6/1942 | Belden | 132/73 |
| 2,941,535 | 6/1960 | Lappe | 132/73 |
| 3,856,026 | 12/1974 | Gaydos | 132/73 |
| 3,928,113 | 12/1975 | Rosenberg | 132/73 |
| 4,222,399 | 9/1980 | Ionescy | 132/73 |
| 4,299,243 | 11/1981 | Umstattd | 132/73 |
| 4,407,310 | 10/1983 | Jadow | 132/73 |
| 4,450,848 | 5/1984 | Ferrigno | 132/73 |

OTHER PUBLICATIONS

Balsam, M. S., Cosmetic's Science and Technology, 1978, pp. 482, 483, 464, and 470, vol. 1.
Sagarin, Cosmetics Science & Technology 1957, pp. 713 and 694.

*Primary Examiner*—Gregory E. McNeill
*Attorney, Agent, or Firm*—Fay, Sharpe, Beall, Fagan, Minnich & McKee

[57] ABSTRACT

A process, requiring minimal skills, for applying a protective acrylic coating, with or without extending the tips, to the human fingernail as afforded by (1) clearing and roughening the surface of the nail, (2) applying a layer of liquid acrylic monomer, (3) applying a powdered polymethacrylate ester to the wetted nail surface, (4) removing loose powder and smoothing the nail surface, (5) brushing on, as one would with nail polish, a second layer of liquid acrylic monomers and, after curing, (6) finishing the nail in the conventional manner.

15 Claims, No Drawings

COMPOSITIONS AND PROCESS FOR APPLYING PROTECTIVE COVERING AND EXTENSIONS TO FINGERNAILS

This is a continuation-in-part application of U.S. patent application Ser. No. 636,987, filed Aug. 2, 1984.

BACKGROUND OF THE INVENTION

The present invention relates to compositions and processes for applying strong protective acrylic coatings to fingernails and toenails with or without artificial extensions to the nails.

Numerous techniques for applying protective coatings for fingernails, with or without extensions to the nails, exist today. The types of artificial nails produced by these techniques can be classified as (1) glue-on nails, (2) nail wraps, (3) sculptured nails, and (4) nail dips.

Glue-ons are pre-formed plastic fingernails having the desired, usually extended shape of the natural nail. These are glued directly on to the fingernail. Because of the wide variety of nail shapes, glue-on nails are difficult to fit. As the nails grow, the glue-on nails move distally creating an unsightly ledge across the base of the nail. This is repaired either by removing the artificial nail and attaching a new one or by filling in behind the ledge by a sculpturing technique as described below. The former repair is expensive because it must be performed every two to three weeks and the removed nail cannot be reused. The latter repair requires the skills of a scupltured nail technician.

In the nail wrap method a piece of paper or fabric is cut to the shape of the natural nail, glue is applied to the natural nail and the paper of fabric is pressed into the glue. The paper or fabric is then smoothed insofar as possible and folded over the free edge of the nail. The folds are glued to the underside of the nail and more glue is applied to the paper or fabric in successive layers until the surface is smooth. This type of artificial nail has many problems. First of all, the nail is made of glues, usually the lower cyanoacrylate esters, which do not produce a particularly strong nail. The single lamina of paper or cloth adds little strength to the composite. Secondly, the surface of the natural nail is a complex curve and it is difficult for the paper or fabric to conform to the surface without forming folds. Under the nail, the folded over paper or fabric forms convolutions which are unattractive when viewed from the edge or from underneath. Moreover, these folds harbor dirt and microorganisms. If edge folds are not used or if the nails are trimmed, the edge is ragged and readily delaminates. As with glue-ons, the artificial nails move distally as the nail grows and must be filled in or the artificial fingernail must be removed and replaced with a new nail wrap.

Nail sculpting has become popular with those who are unsatisfied with the methods described above. However, nail sculpting requires a great deal of training and skill. In this method, preparation of the natural nail is important because the thick, tough acrylic nail becomes permanently attached to the point where it is applied. The nail is first cleaned, roughened, and treated with a bromide. It is then coated with glue, usually a cyanoacrylate ester, or a primer containing methacrylic acid which binds the acrylic to the natural nail. Then the sculpturist wets a small brush with a liquid consisting of a blend of mono-, di- and trimethacrylate esters and a promoter, usually N, N, dimethyl-para-toluidine which is capable of inducing the decomposition of benzoyl peroxide at room temperature. The wetted brush is then dipped into a finely powdered polymethacrylate ester which contains benzoyl peroxide. The liquid and powder form a dough which begins to cure (i.e., harden or polymerize) immediately. The dough is then quickly placed onto the prepared nail and smoothed or sculptured in place. More dough is added until the nail is covered and filled to the desired, uniform thickness and shape. Filing, buffing and, sometimes, the addition of more dough result in a strong, albeit thick nail ready for polish. If the fingernail is to be extended, a form with a non-adhering upper surface is placed under the edge of the nail and the sculpturing is continued out over the form. The form is removed after the dough is cured.

Extraordinary skills are required for this procedure. The dough must be of a precise consistency. If it is too thin, it is runny and cures slowly and sometimes does not cure at all. If it is too thick, it is weak due to air bubbles and stress cracks. If the sculpturist pauses too long between applying each brush full of dough, the bond is poor and the nail cracks essily. If the dough is not placed and worked skillfully an excessive amount of filing is required to remove humps and lumps to produce an attractive nail.

Recently, a method of applying artificial fingernails called nail dipping has been introduced. In this method, the natural nail is coated with a high-viscosity glue of the cyanoacrylate ester type. The wetted nail is then briefly dipped into a powdered, uncross-linked polymethacrylate ester. Any excess powder is brushed off and the surface is smoothed partially by filing and light buffing. This rough surface is then sealed or filled in by applying a low-viscosity cyanoacrylate ester glue in one or more coats until the powder no longer protrudes above the surface. The surface is then filed and buffed and is ready for the application of nail polish.

It is apparent that this method circumvents the fitting problems of glueing-on and wrapping and the skills required of sculpting. However, the finished nail is not strong. The cyanoacrylate ester glues, although adherent, are not structurally sound. Layers as thick as artificial nails if not supported by opposing substrates break easily. The uncross linked polyethylmethacrylate powder is weak per se and lends little toughness to the polycyanoacrylate ester surrounding it. Thus, the dip process nail may be stronger than nail polish but it is much weaker than a sculpted acrylic nail.

It follows, therefore, that there is a present need for strong, easily appliable, repairable, fillable, artificial nails and a better procedure to repair and strengthen natural nails and to apply the artificial nails.

SUMMARY OF THE INVENTION

It is the object of this invention to provide a new method for applying artificial fingernails and repairing and strengthening natural fingernails which neither requires the extraordinary skills of the sculpturing method nor presents the fitting problems of the wrapping and glue-on methods. It is a second but not lesser object of this invention to provide compositions of matter which are essential to the success and simplicity of this new method while providing a protective artificial nail or nail coating having excellent strength and a glossy surface which, imparts a gloss or wet look to ordinary fingernail polishes applied thereto.

The procedure and compositions are described as follows with the understanding that this description should not be construed as limiting the scope of our invention but should be considered as examples thereof.

As in the application of any artificial fingernail the first step is the proper preparation of the surface of the natural nail. All traces of nail polish and residues of previous artificial nails are removed with an oilless nail polish remover and a glue and nail solvent respectively. Glue and nail solvents preferably contain major portions of acetonitrile, methylene chloride, acetone, ethyl acetate and closely homologous solvents such as propionitrile, 1, 1, 1-trichloroethane, butan-2-one, methyl acetate and butyl acetate. In particular, we have found that solvents for cyanoacrylate ester glues should contain at least 90 vol % acetonitrile if the remainder is a non-solvent such as water, isopropanol or such hydrocarbons as mineral spirits or toluene. Similarly, the ketones such as acetone and the few non-hazardous chlorocarbons such as methylene chloride should not be diluted more than 30% with non-solvents such as were mentioned above. The esters such as ethyl and butyl acetates are slower to dissolve cyanoacrylate ester polymers and should not be diluted with non-solvents at all. However, the better solvents such as acetonitrile, acetone and methylene chloride can be mixed in any proportion with one another to provide fast and effective solvents for cyanoacrylate ester polymers. Many other organic liquids such as the N-alkyl and N,N-dialkyl formamides and acetoamides and certain esters such as tetrahydrofuran are effective solvents for cyanoacrylate ester glues from a mechanical standpoint but their toxological properties are in doubt and should not be considered until their safety is proven.

EXAMPLES

The following solvents are useful for removing artificial nails which are attached with glues.

TABLE I

| Component | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| Acetonitrile, vol % | 100 | 94 | 90 | 90 | 50 | 50 |  | 34 |  |  |  |  |  | 50 |  | 25 |
| Acetone, vol % |  |  | 6 |  | 50 |  | 50 | 33 | 100 |  |  |  |  | 50 | 40 | 25 |
| Methylene chloride, vol % |  |  |  |  |  | 50 | 50 | 33 |  | 100 |  |  |  |  | 30 | 25 |
| Butan-2-one, vol % |  |  |  |  |  |  |  |  |  |  |  |  | 25 |  |  |  |
| Methyl acetate, vol % |  |  |  |  |  |  |  |  |  |  | 50 | 25 |  |  |  |  |
| Ethyl acetate, vol % |  |  |  |  |  |  |  |  |  |  |  | 25 |  |  |  | 10 |
| Isopropyl acetate, vol % |  |  |  |  |  |  |  |  |  |  |  | 25 |  |  |  |  |
| N—Butyl acetate, vol % |  |  |  |  |  |  |  |  |  |  | 50 | 25 |  |  |  | 10 |
| Propionitrile, vol % |  |  |  |  |  |  |  |  |  |  |  |  | 50 |  |  |  |
| 1,1,1-trichloroethane, vol % |  |  |  |  |  |  |  |  |  |  |  |  |  |  | 30 |  |
| Methyl isobutylketone, vol % |  |  |  |  |  |  |  |  |  |  |  |  | 25 |  |  |  |
| Water, vol % |  | 6 | 4 |  |  |  |  |  |  |  |  |  |  |  |  |  |
| Odorless mineral spirits, vol % |  |  |  | 5 |  |  |  |  |  |  |  |  |  |  |  | 5 |
| Toluene, vol % |  |  |  | 5 |  |  |  |  |  |  |  |  |  |  |  |  | bornanone, cineole, safrole, bornyl chloride, 2-phenoxyethanol, benzyl alcohol and ethanol.

It is sufficient that no more than 1% by weight of any one of the above named biocides and no more than 2% total of all of the above named biocides be employed in water-free solutions because the solvents evaporate after the solution is spread the nail, leaving the active biocides as a thin film on the nail at a total concentration of essentially 100%.

It is preferred that as many different biocidal compounds be used together as is practicable. Each biocide has a "map" of effectiveness against bacteria, yeasts and fungi. Not even the most effective antibiotics have a map which encompasses all microorganisms, e.g., one might be effective against Gram-positive bacteria only whereas another might be effective against Gram-negative bacteria only. Thus, to kill the greatest number of species of microorganisms, one should employ the greatest number of biocides restricted only by practicality, compatability, and kill map overlap.

The preferred acidic biocidal compounds include thymol, chlorothymol, benzoic acid, the p-hydroxybenzoate alkyl esters, 4- and 6-phenyl-2-chlorophenyl, carvocrol and (the FDA regulated compound) hexachlorophene, should it be allowed for use on fingernails.

There are many other biocidal compounds which perform very well in this application from a technical standpoint but which have practical limitations such as color in the case of the nitroforans, odor in the case of allicin, irritation in the case of 2-phenylphenol, insolubility in the cases of boric acid and sodium benzoate, toxicity in the case of the mercurials and both cost and regulations in the cases of such antibiotics as Bacitracin and Griseofulvin. They are, however, considered to be within the scope of our invention.

We have found that the solvent blend for our biocides

After the nail has been cleaned, a water-free solution of biocides is applied to prevent or inhibit the growth of bacteria, yeast and fungi between the artificial and natural nails. Of the few non-perscription, non-toxic, non-irritating, non-hygroscopic, organic soluble, effective biocides available for this purpose, some are acidic or phenolic. These include benzoic acid, thymol and the para-hydroxybenzoic esters.

We have found that certain combinations of non-acidic antimicrobial agents in certain water-free blends of organic solvents provide protection against growth of bacteria, yeasts and fungi without affecting the cure rate or the bond strength of the glue layer. The biocides include the quarternary ammonium halides such as n-alkyldimethylbenzylammonium chloride, cetyl pyridinium bromide, 5-methyl-2-isopropyl-cyclohexanol, 2- should have the following six qualities; (1) volatility sufficient to evaporate quickly from the nail, (2) solvency for natural body oils and oils and greases customarily used in cosmetics, (3solvency for water but not hygroscopic, (4) low viscosity so that it can penetrate the upper cellular layers of the fingernail, (5) water azeotropy and (6) solvency for all of the biocides.

The combined said qualities enable the solvent to place the biocides both on and deeply into the nail and at the same time carry bond-destroying oils and some superfluous water deep into the nail. Additional superfluous water is removed by co-evaporation. Only quasi-chemically bound water remains on the surface of the nail along with that fraction of the biocides which did not penetrate into the upper cell layers.

Such solvents include especially acetone, methyl acetate and ethyl acetate, alone or in admixture, for fastest evaporation and best penetration. Evaporation and penetration can be retarded, as desired, by the addition of higher boiling and more viscous solvents such as ethanol, 1-propanol, 2-propanol, butan-2-one, pentan-2-one, pentan-3-one, methyl isobutyl ketone, n-propyl acetate, isopropyl acetate, n-butyl acetate, isobutyl acetate and sec-butyl acetate. Typical blends would include (1) 75 vol % acetone, 20 vol % methyl acetate and 5 vol % ethanol (2) 60 vol % acetone, 39 vol % ethyl acetate and 1 vol % ethanol, (3) 50 vol % acetone, 30 vol % ethyl acetate, 10 vol % butan-2one, 5 vol % n-butyl acetate and 5 vol % ethanol and (4) 80 vol % acetone, 19.5 vol % methyl acetate and 0.5 vol % ethanol, the last being added as a component of commerically available solutions of quarternary ammonium salts such as n-alkyldimethylbenzyl-ammonium chloride.

When applying the acrylic nail of this invention it is best to use a biocide without acidic components. The biocidal solution can be applied either before or after roughening the nail by the liquid abrasive of this invention described below because the liquid abrasive does not introduce new microorganisms as would a rigid filing device such as an emery board.

The next step in the preparation of the natural nail for applying the artificial nail of this invention consists of roughening the nail to provide physical interlocking of the natural nail with the glue and to present a surface of fresh, chemcially bound protein instead of partly decomposed protein in the process of becoming chemically debonded.

The preferred roughness for applying artificial nails is not that produced by sandpaper or an emery board such that the scratches are visible to the naked eye. This process leaves loosened high ridges and shards which break away easily and provide caverns for entrapment of air which weakens the bond between the glue and the natural nail. In addition, these roughening devices are harsh and potentially injurious to the skin around the nail.

We have found that suspensions of finely divided inorganic minerals and salts in volatile organic solvents or water when rubbed briskly over the natural nail will remove the "shine" from the nail and leave a matte finish which forms an excellent bond.

Since the natural nail is very soft almost any mineral with a measurable hardness on the Moh scale will suffice. Talc (Mol hardness about 1.0) produces a roughened surface after only a few seconds of rubbing. Other suitable minerals include kaolin, gypsum, calcite, dolomite, magnesite, wollastonite, diatomaceous earth, fumed silica, powdered silica, garnet, spinel, pumice, corundum and zinc oxide.

Generally the mineral particle size should be smsller than 80 mesh and preferably smaller than 100 mesh. Even fumed silica with paticle sizes below 0.01 microns provides a nail surface which bonds satisfactorily.

The suspending liquid is preferably one which evaporates quickly enough to enable the operator to proceed to the next step without waiting. Generally, the lower members of the homologous series of alcohols ketones and esters are preferred. Water is satisfactory but it takes too long to evaporate in humid weather. Other organic compounds such as the nitropropanes and odorless mineral spirits are satisfactory from a technical standpoint but some customers do not like the oily "feel" of these liquids.

The lower alcohols have a special advantage (besides being antiseptic) in that they do not dissolve synthetic fabrics. The supending liquid could spill onto the garments of the operator or the customer and dissolve or fuse the synthetic fabrics if the liquid contained major portions of ketones or acetate esters. Also, cotton balls which are useful matrices for applying the buffing mixture are sometimes made of blends of cotton and synthetic fibers. Such a matrix would become tacky and fused when saturated with a ketone or ester and leave plastic deposits on the nails of the customer and the fingers of the operator. Thus, if an operator were to use a buffing liquid composed chiefly of ketones or esters, she or he must use buffing matrices made only of natural materials. This problem is relieved if the ketones or esters are diluted with non-solvents. For example, 80 vol % acetone and 20 vol % water or 70% ethyl acetate and 30% odorless mineral spirits do not significantly attack the cottonpolyester blends currently used in the manufacture of cotton balls.

Numerous matrices are suitable for applying the roughening suspension to the natural nail. Cotton balls, small pieces of towel, sponges, foamed soft plastics and even the finger can be used.

EXAMPLES

The following buffing media were prepared by addition with agitation of the solids, measured by weight, to the liquids, measured by volume (or the reverse procedure) followed by adjustment of the pH to slightly alkaline if necessary.

TABLE II

| Component | Example # | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Butyl acetate, ml | 20 | 10 | | 15 | 10 | | | | | | | | | |
| Ethyl acetate, ml | | | 5 | | | | | | | | | | | |
| Ispropyl alcohol, ml | | 10 | | 20 | | | 15 | 20 | 10 | 12 | | 20 | 10 | 20 |
| Water, ml | | | | | | 20 | | | | | 8 | | | |
| Isoamyl acetate, ml | | | 20 | | | 10 | | | | 10 | | | | |
| Acetone, ml | | | | | | | 5 | | | | | | | |
| Fumed silica M-5*, g | 1.0 | | | | | | 1.2 | | | | | 1.5 | | |
| Fumed silica EH-5*, g | | 1.0 | | | | | | | | | 0.7 | | | |
| Talc, >100 mesh, g | | | | 1.0 | 2.0 | 0.5 | | | | | | | | |
| Kaolin >100 mesh, g | | | | | | | 1.5 | | | | | | | |
| Diatomaceous earth, g | | | 1.0 | | | | | | | | | | 1.0 | |
| Pumice, >100 mesh, g | | | | | | | | | 0.8 | | | | | |
| Corundum, >100 mesh, g | | | | | | | | | | 0.6 | | | | |

TABLE II-continued

| Component | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Triethanolamine, ml | .03 | .035 | .2 | | | | .04 | | | | .02 | .045 | | |
| Zinc Oxide, g | | | | | | | | | | | | | | 4 |

*Grade designation of Cab-O-Sil mfd. by Cabot Corp.

The next step is the application of a layer of liquid metacrylate monomer blend. This blend contains a promotor, usually N,N-dimethyl-p-toluidine, to initiate decomposition of the benzoyl peroxide in the powder described below. This monomer blend also contains one or more dissolved polymers and/or inorganic fillers to increase the viscosity to approximately that of fingernail polishes. This enables the user to apply acrylic monomers with the ease of applying nail polish. The monomer blend consists of three major parts A, B and C. Part A is composed preferably as follows:

TABLE III

| Components | Usable Range, Vol % | Preferred Vol % |
|---|---|---|
| Ethyl methacrylate | 30–90 | 50–75 |
| Isobutyl methacrylate | 1–50 | 5–15 |
| Trimethylolpropane trimethacrylate | 2–20 | 5–15 |
| PEG 200 dimethacrylate | 1–10 | 2–7 |
| Hydroxyethylmethacrylate | 0.001–1.0 | .01–0.5 |
| N,N—dimethyl-p-toluidine | .1–6.0 | .5–3.0 |
| D + C Violet #2 (w/v, gms/m/of A) | .0001–0.1 | .001–.02 |
| Cyasorb UV 5411 ® (w/v, gms/m/of A) | .0001–0.1 | .001–.02 |

Ethylmethacrylate is the major monomer of Part A. If less than 30 vol. % of this monomer is used, the fingernail produced will be too soft. Since ethylmethacrylate has a strong odor, odorless isobutylmethacrylate is added to the monomer blend to prevent the odor from being too strong. However, if the monomer blend contains more than 50 vol % of isobutylmethacrylate, the nail produced is too soft. Trimethylopropane trimethylmethacrylate is the preferred cross-linker for this blend and produces an extremely hard nail but, because of its expense, no more than 20 vol % is used. This blending may be perfumed as desired. The Drug & Cosmetic (D & C) Violet #2 dye is added as a 0.1–1.0% (w/v) solution in hydroxyethyl methacrylate to obscure any yellowing in the acrylic nail. Other ethylene glycol ether dimethacrylates such as ethylene glycol dimethacrylate, di-, ti- and tetra-ethylene glycol dimethacrylates and blends thereof may be substituted for polyethylene glycol (PEG) 200 dimethacrylate which is used to compatablize the violet dye. Hydroxyethylmethacrylate is used as a solvent for the violet dye. Cyasorb UV-5411 ® is an ultraviolet light absorber added to protect the fingernail against yellowing and cracking with the passage of time. Other ultra-violet absorbers such as solol, benzophenone-1, benzophenone-6, Cyasorb UV-9 ®, may be substituted for Cyasorb UV-541 that portions of the artificial nails or nail coatings according to the present invention can be in place approximately six months.

Other monomer blends may be used in the process of this invention, the blend:
Isobutylmethacrylate, 75–95 vol %
Ethylene glycol dimethacrylate, 5–25 vol %
N,N-dimethyl-para toluidine, 0.5–8.0 vol %
has the advantage of low odor although the nail is softer than most wearers prefer.

For a very hard nail, the blend:
Methyl methacrylate, 90–98 vol %
Trimethylolpropane trimethacrylate, 1–10 vol %
N,N-dimethyl-para-toluidine, 0.2–2.0 vol %
is well suited from a technical standpoint. However, the USFDA presently prohibits the use of methylmethacrylate in artificial fingernails for interstate commerce. Should this prohibition be removed blends containing methylmethacrylate would be preferred for extra-hard artificial nails.

Part B is one or more non-reactive or "dead" polymers and is used for the purpose of increasing viscosity. It is added to part A in the proportion of 2–40 g per 100 ml and preferably 5–25 g. Classes of polymers suitable for this application include the cellulose esters, toluenesulfonamide-formaldehyde condensation polymers, polyesters of the diol terephthalate group, polyvinyl acetals especially polyvinyl butyrol, nylons, polycarbonates, terminated polymethacrylates and polyurethanes. Molecular weight ranges should be selected such that the polymers are soluble in methacrylate esters but still have strength properties equal to or greater than the cured part A. Cellulose acetate butyrate is preferred.

Part C consists of inorganic powders added to part A in the proportion of 0.5–20 g of C per hundred ml. of part A and preferably 1.0–10 g. It is preferred that the high viscosity of the monomer blend not be achieved entirely with dissolved polymers which interfere with the curing of the monomers. We have found that part of the desired flow property can be obtained with fine inorganic powders, at least finer than 200 mesh and preferably finer than 325 mesh. Neutral to slightly alkaline minerals and inorganic salts which do not interfere with the monomerpromoters include talc, the kaolins, Fuller's earth, wollastonite, gypsum and dolomite, inter alia.

Before the monomer blend cures, a powdered polymethacryate ester, to which has been added benzoyl peroxide, is applied to the wet surface. This should be done about three seconds after the monomer blend is applied.

The polymethacrylate ester is preferably polyethylmethacrylate or copolymers of ethyl methacrylate with methylmethacrylate or isobutylmethacrylate but containing no more than 50% of these other co-monomers. As manufactured by the conventional suspension polymerization process, the polymer contains trace amounts of residual benzoyl peroxide as well as free radical chain termini which are chemically reactive toward acrylic and methacrylic esters. Also, these polymethacrylates are naturally produced in particle sizes from about 60 mesh/inch to finer than 325 mesh. We have found that these polymers are improved for the purposes of this invention by removing all particles larger than 80 mesh, by restricting particles larger than 100 mesh to less than 5% by weight and by adding an additional 1–8% and perferably 3–6% of benzoyl peroxide. If less than 3% benzoyl peroxide is present in the powder, the nail cures too slowly to be practical in a salon. Also, it might not cure at all. If more than 8% benzoyl peroxide is present, the finished nail contains too many low molecular weight polymers and is brittle (if highly cross-linked) or ranges from soft to tacky. The benzoyl peroxide should be thoroughly blended with the polymer and should have a particle size of less than 100 mesh. A benzoyl peroxide Lupersol AA, manufactured by the Pennwalt Corporation has been found to be satisfactory for the practice of this invention. The use of other forms of benzoyl peroxide such as sprayed-on acetone solutions and the use of percentages and particle sizes outside of the preferred values should be regarded as personal preference and within the scope of this invention.

When the powder is applied to the wet nail the polymer instantly sticks to the glue. Loose powder is brushed off. The powdery surface is then buffed lightly to remove any protrusions difficult to cover in the subsequent steps and also to insure that the surface of the powder is fresh, that is, free of skin oils, and contains the maximum surface population of benzoyl peroxide and free radicals.

This surface should not be touched. If it is, it should be buffed again to re-expose fresh surface.

The buffing of the powdered surface can be accomplished with any of the commercially available fine sanding or buffing pads or with a fine-grained every board.

After buffing is complete, the powder is coated with a second layer of methacrylic monomers blend. This acrylic coating begins to cure immediately by the combined actions of the promoter, benzoyl peroxide and live polymer termini on the methacrylic monomers. As soon as this coating is no longer tacky, a second coating of the same material may be applied if a thicker nail is desired. Optionally, the second coating can be a similar blend of methacrylic esters containing one or more inorganic fillers and lesser amounts of dissolved polymer such that the second coat has the flow properties of a "ridge filler" and generates a smooth surface, or the second coating can be a commercially available ridge filler or base coat.

After the acrylic coat is hard, it is filed smooth and buffed. Application thereafter of ridge filler (if necessary) base coat, polish and top coat is carried out in the conventional manner.

EXAMPLES

Fingernails according to the process and compositions of the present invention were prepared as follows:
1. The nails were cleaned and remnants of polish, old glue and previous artificial fingernails were removed using a solvent comprising 96% acetonitrile.
2. A biocide solution comprising a solvent essentially consistig of 80by volume acetone and 20% by volume methyl acetate to which is added 0.05-2.0% by volume of biocide, was applied to each nail.
3. The cuticle at the base of the nail was pushed back and the surface of the natural nail was roughened with an abrasive suspension comprising two grams of talc having a particle size smaller than 100 mesh and suspended in 20 ml of isopropyl alcohol.
4. A layer of liquid methacrylate monomer blend was brushed on said blend comprising:

| Components | Preferred Vol % |
| --- | --- |
| Ethyl methacrylate | 50–75 |
| Isobutyl methacrylate | 5–15 |
| Trimethylolpropane trimethacrylate | 5–15 |
| PEG 200 dimethacrylate | 2–7 |
| Hydroxyethylmethacrylate | .01–0.5 |
| N,N—dimethyl-p-toluidine | .5–3.0 |
| D + C Violet No. 2 (w/v, g/ml of A) | .001–.02 |
| Cyasorb UV 5411 (w/v, g/ml of A) | .001–.02 |

To each 100 ml of this monomer blend was added 5-25 grams of cellulose butyrate acetate and 0.0 to 10 grams of talc.

5. After about 2 to 5 seconds, the wet surface of the glue covered nail is inverted and rested onto or pressed into a finely powdered polymethacrylate ester wherein the particle size is smaller than 80 mesh and further wherein particles larger than 100 mesh comprise less than 5% by weight of the polyethylenemethacrylate ester. This powder also contains 3-6 weight % benzoyl peroxride catalyst having a particle size less than 100 mesh. The fingernail remains applied to the surface of the powder for just an instant.
6. The fingernail coated with polymethacrylate ester powder was brushed to remove loose powder.
7. The adhering powder was filed, sanded and buffed lightly to remove high spots and expose a fresh catalyst surface. The surface was brushed again to remove loose powder.
8. The liquid blend of methacrylate was again brushed on to the surface of each nail in the manner of applying nail polish.
9. After hardening, the surface was filed, sanded, buffed and/or smoothed and was ready for the conventional application of one or more ridge fillers, base coats, polishes, top coats and/or dryers.

The resulting fingernails were thinner and more graceful than sculptured nails and had the form and shape of the wearer's natural nails. Unlike the nail dip process, this surface was hard and durable and nail polish applied thereto does not chip off. Moreover, the surface of the polished nail has a high gloss or wet look. As the natural nail grows, an uncovered portion of the natural nail becomes increasingly visible. This portion can easily be filled in using the above process and composition.

The same process and compositions above were applied to fingernails which had been artificially extended by adhering an artificial to the edge of the nail. The same beneficial results were observed.

The fingernails produced according to the process compositions of the present invention present many benefits and advantages not obtained with the four types of artificial fingernails described above. In particular, this process is relatively simple and does not require the high level of skill necessitated by the glue-on, nail wrap and sculptured nail processes. Also, if mistakes are made in the process of the present invention, they are easily correctable since the compositions, including an applied artificial fingernail can be removed by an application of the glue and nail solvent used in step 1 above. In the four cited prior art processes, mistakes are usually filed or cut off.

Liquid coatings used in the prior art processes often spattered onto the skin surrounding the fingernail and caused a burning sensation. Sometimes the wearer's fingers became bonded together and there was some likelihood that the manicurist's skin could become bonded to that of the wearer. To avoid these problems, applicant's first of all insured that the viscosity of both the glue and the monomer blend would be high enough for the composition to remain on the nail and not run onto the surrounding tissue. Also, solution does get on the skin, it is easily removed by an application of the solvent.

While the present invention has been specifically described with respect to examples, each with variations employable with the others and modifications, for the specific features of the present invention, they also indicate a breadth for the broader aspects of the present invention, so that the present invention includes both the specific elements and further embodiments, modifications and variations not disclosed, all within the spirit and scope of the following claims.

We claim:

1. A process for applying a protective acrylic coating, to the human fingernail comprising:
   (a) cleaning the nail with an oil-free nail polish remover follower by cleaning with a solvent containing at least one of the groups consisting of acetonitrile, methylene chloride, acetone, ethylacetate, proprionitrile, 1,1,1-trichloroethane, butane-2-one, methylacetate and butylacetate;
   (b) roughening the surface of the nail;
   (c) applying a layer of liquid methacrylic monomer blend to the surface of the nail;
   (d) applying a layer of powder comprising polymethacrylic ester to the surface of the liquid while still wet;
   (e) applying a second layer of a liquid methacryate monomer blend to the surface produced by step (d);
   (f) curing the coating produced by step (e); and
   wherein after the nail cleaned, a water free solution of biocide is applied, said biocide being at least one selected from the group consisting of n-alkyldimethylbenzylammonium chloride, cetyl pyridinium bromide, 5-methyl-2-isopropyl-cyclohexanol, 2-bornanone, cineole, safrole, bornyl chloride, 2-phenoxyethanol, benzyl alcohol, ethanol, thymol, chlorothymol, benzoic acid, p-hydroxybenzoate alkyl esters, 4-and 6-phenyl-2-chlorophenol, carvacrol and hexachlorophene.

2. A process according to claim 1, wherein the solvent comprises 96% by volume acetonitrile.

3. A process according to claim 1, wherein a solvent for the biocide solution is at least one of the group consisting of acetone, methylacetate, ethylacetate, ethanol, 1-propanol, 2-propanol, butan-2-one, pentan-2-one, pentan-3-one, methyl isobutyl ketone, n-propyl acetate, isopropyl acetate, n-butyl acetate, isobutyl acetate, and sec-butyl acetate.

4. The process according to claim 3 wherein the solvent for the biocide solution is at least one of the group consisting of acetone, methylacetate and ethylacetate.

5. The process according to claim 4, wherein the solvent for the biocide solution is 80% acetone and 20% methylacetate by volume.

6. The process according to claim 4, wherein the roughening step is performed by briskly rubbing with an abrasive suspension containing at least one of talc, kaolin, gypsum, calcite, dolomite, magnesite, wollastonite, diatomaceous earth, fumed silica, powdered silica, garnet, spinel, pumice, corundum, and zine oxide suspended in at least one of volatile organic solvents and water.

7. A process according to claim 6 wherein, the abrasive suspension comprises 2 g of talc suspended in 20 ml of isopropyl alcohol.

8. The process according to claim 4, wherein the powder applied in step (d) comprises at least one of polyethylmethacrylate, copolymers of ethylmethacrylate with methylmethacrylate and copolymers of ethylmethacrylate with isobutylmethacrylate, having a particle size smaller than 80 mesh wherein said powder contains no more than 5% by weight of particles larger than 100 mesh.

9. The process according to claim 8, wherein said powder also contains 1-8% by weight and preferably 3-6% of benzoyl peroxide, said benzoyl peroxide having a particle size of less than 100 mesh.

10. A process according to claim 4, wherein after step (d) and before step (e), loose powder not adhered to the surface of the glue is brushed off and the resulting surface is then buffed lightly.

11. A process according to claim 4 wherein after step (e), the fingernail is at least one of filed, sanded, buffed and smoothed.

12. A process according to claim 4, wherein before step (a) is performed, an artificial fingernail tip is applied to the free edge of the fingernail to artificially extend said nail.

13. A process for applying a protective acrylic coating, to the human fingernail comprising:
   (a) roughening the surface of the nail;
   (b) applying a layer of liquid methacrylic monomer blend to the surface of the nail;
   (c) applying a layer of powder comprising polymethacrylic ester to the surface of the liquid while still wet;
   (d) applying a second layer of a liquid methacryate monomer blend to the surface produced by step (c);
   (e) curing the coating produced by step (d);
   wherein the monomer blend comprises three parts, A, B and C and further wherein part A comprises:
   3014 90 vol % of Ethyl methacrylate,
   1-50 vol % of Isobutyl methacrylate,
   2-20 vol % of Trimethylolpropane trimethacrylate,
   1-10 vol % of PEG 200 dimethacrylate,
   0.001-1.0 vol % of Hydroxyethylmethacrylate,
   0.1-6.0 vol % of N,N-dimethyl-toluidine,
   0.0001-0.1 g/ml of total A D+C Violet #2,
   0.0001-0.1 g/ml of total A cyasorb UV 5411;
   part B is one or more non-reactive polymers selected from the group consisting of cellulose esters, toluene-sulfonamide-formaldehyde condensation polymers, polyesters of the diol terephthalate group, polyvinyl acetals, nylons, polycarbonates, terminated polymethacrylates and polyurethanes, wherein part B is provided in the range of 2-40 g per 100 ml of part A and preferably 5-25 g, and
   part C is at least one selected from the group consisting of talc, kaolin, gypsum, Fuller's earth, dolomite and wollastonite provided in an amount of 0.5-20 g of C per 100 ml of part A and preferably 1-10 grams per milliliter, and
   having a particle size smaller than 80 mesh and containing no more than 5% by weight of particles larger than 100 mesh.

14. A process according to claim 13, wherein before step (a), the nail is cleaned with an oil-free nail polish remover followed by cleaning with a solvent containing at least one of the groups consisting of acetonitrile, methylene chloride, acetone, ethylacetate, proprionitrile, 1,1,1,-trichloroethane, butane-2-one, methylacetate and butylacetate.

15. The process according to claim 13, wherein part A comprises:

Ethyl methacrylate: 50–75
Isobutyl methacrylate: 5–15
Trimethylolpropane trimethacrylate: 5–15
PEG (polyethylene glycol) 200 dimethacrylate: 2–7
Hydroxyethylmethacrylate; 0.01–0.5
N,N-dimethyl-p-toluidine: 0.5–3.0
D+C Violet No. 2 (g/ml of A): 0.001–0.02
Cyasorb UV 5411 (g/ml of A): 0.01–0.02.

* * * * *